(12) United States Patent
Divi et al.

(10) Patent No.: US 8,080,670 B2
(45) Date of Patent: Dec. 20, 2011

(54) PROCESS FOR THE PREPARATION OF IRBESARTAN

(75) Inventors: Murali Krishna Prasad Divi, Andhrapradesh (IN); Mysore Aswatha Narayana Rao, Andhrapradesh (IN); Surendra Kalyan Nuthi, Andhrapradesh (IN); Yugandar Phaniram Bandaru, Andhrapradesh (IN)

(73) Assignee: Divi's Laboratories, Ltd. (IN)

( * ) Notice: Subject to any disclaimer, the term of this patent is extended or adjusted under 35 U.S.C. 154(b) by 27 days.

(21) Appl. No.: 12/819,713

(22) Filed: Jun. 21, 2010

(65) Prior Publication Data

US 2011/0275828 A1 Nov. 10, 2011

(30) Foreign Application Priority Data

May 4, 2010 (IN) .......................... 1249/CHE/2010

(51) Int. Cl.
*C07D 249/00* (2006.01)
(52) U.S. Cl. .................................. 548/300.1; 548/301.1
(58) Field of Classification Search ............... 548/300.1, 548/301.1
See application file for complete search history.

(56) References Cited

U.S. PATENT DOCUMENTS

| 5,270,317 A | 12/1993 | Bernhart et al. |
| 5,629,331 A | 5/1997 | Caron et al. |

FOREIGN PATENT DOCUMENTS

| EP | 1918288 A1 | 5/2008 |
| WO | 2005051943 A1 | 6/2005 |
| WO | 2005/113518 | * 12/2005 |
| WO | 2005113518 A1 | 12/2005 |
| WO | 2007013101 A1 | 2/2007 |
| WO | 2008010779 A2 | 9/2008 |

OTHER PUBLICATIONS

P.R. Bernstein and E.P. Vacek, Improved Conditions for the Formation of Tetrazoles, Medicinal Chemistry Department, Synthesis, 1987, 1133-1134.

* cited by examiner

*Primary Examiner* — Susannah Chung
(74) *Attorney, Agent, or Firm* — Caesar, Rivise, Bernstein, Cohen & Pokotilow, Ltd.

(57) ABSTRACT

The present invention relates to a process for the preparation of 2-butyl-3-[[2'-(1H-tetrazol-5-yl)[1,1'-biphenyl]-4-yl]-1,3-diazaspiro[4,4]non-1-en-4-one by reaction of the corresponding nitrile with sodium azide and piperazine or its acid salt.

5 Claims, No Drawings

US 8,080,670 B2

PROCESS FOR THE PREPARATION OF IRBESARTAN

FIELD OF INVENTION

The present invention discloses an improved process for the preparation of irbesartan, an angiotensin-II receptor antagonist used for the treatment of hypertension.

BACKGROUND OF THE INVENTION

Irbesartan is chemically, 2-butyl-3-[[2'-(1H-tetrazol-5-yl)[1,1'-biphenyl]-4-yl]-1,3-diazaspiro[4,4]non-1-en-4-one and is represented by the Formula I

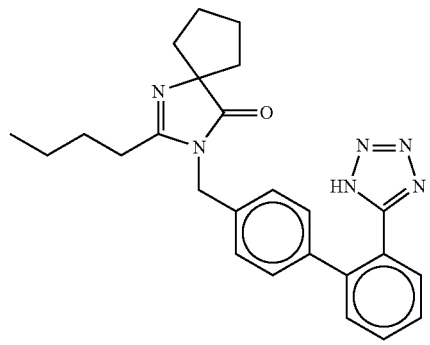

Formula I

Irbesartan and its use in treating hypertension were first disclosed by Bernhart et al in U.S. Pat. No. 5,270,317 and assigned to Sanofi. The process for the preparation of irbesartan described in '317 patent involves the formation of tetrazole ring by a reaction of the cyano intermediate (Formula II) with tributyltin azide.

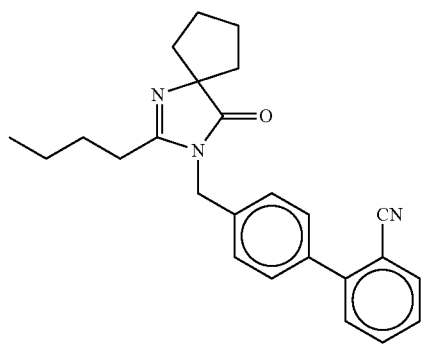

Formula II

The '317 process yields irbesartan of low purity and requires purification by column chromatography.

The application WO 2005/113518 describes a process for irbesartan where the cyano intermediate (Formula II) is reacted with tributyltin chloride and sodium azide. The application WO 2005/051943 describes a process using tributyltin chloride, sodium azide and tetrabutyl ammonium bromide (TBAB) to prepare irbesartan. The use of tributyltin reagents results in a product with high content of tin and requires extensive purification steps.

The patent EP 1918288A1 describes a process for the preparation of irbesartan which involves the reaction of the cyano intermediate with sodium azide and zinc chloride. Irbesartan obtained by using zinc chloride was found to contain significant amounts of 2-n-butyl-3-[(2'-carboxamidobiphenyl-4-yl)methyl]-1,3-diazaspiro-[4,4]-non-1-en-4-one (Formula-III) as an impurity. The removal of this impurity requires extensive purification resulting in considerable yield loss.

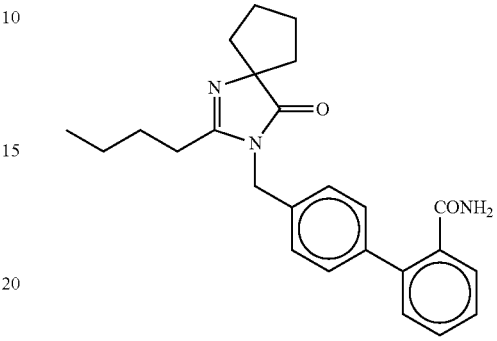

Formula.III

Synthesis of tetrazole moiety from a cyano compound using sodium azide and triethylammonium chloride in DMF is reported in the literature (Synthesis, 1987, 1133-1134). The U.S. Pat. No. 5,629,331 also describes a process for irbesartan where the cyano intermediate is reacted with sodium azide and methyl ammonium chloride in 1-methyl pyrrolidin-2-one as a solvent. Irbesartan obtained by this method does not have satisfactory purity and also contains the 2-n-butyl-3-[(2'-carboxamidobiphenyl-4-yl)methyl]-1,3-diazaspiro-[4,4]-non-1-en-4-one (Formula-III) as an impurity. Extensive purification is required for the removal of this impurity. The solvent used is also expensive. PCT application WO 2007/013101 describes the use of triethylamine and acetic acid in place of triethylammonium chloride. However, it is reported in NO 2008/107799 that the Irbesartan obtained by the process described in the '101 application does not have satisfactory purity and the process produces poor product yield. Moreover the processes using triethylammonium chloride require long times of reaction and yet result in incomplete conversion.

Thus the processes described in the prior art are not satisfactory on an industrial scale. There is a need for an improved process for the preparation of irbesartan that is economical and results in high purity of the product.

SUMMARY OF THE INVENTION

Because of the drawbacks associated with triethylamine hydrochloride such as incomplete reaction and long reaction time, the present inventors screened a large number of amines and their acid salts, such as diethylamine, piperidine, N-methylmorpholine, triethanolamine, piperazine and quaternary ammonium halides, such as tetramethylammonium bromide etc. Some of the tested amines effected significant conversions of the nitrile to the tetrazole, but overall reaction time and purity of product were similar to the results with triethylamine hydrochloride. However, we found that piperazine or its acid salt are excellent catalysts in the reaction of sodium azide with cyano intermediate (Formula II) resulting in irbesartan of high purity.

In another embodiment, the present invention provides a process for irbesartan where the impurity, 2-n-butyl-3-[(2'-carboxamidobiphenyl-4-yl)methyl]-1,3-diazaspiro-[4,4]-non-1-en-4-one (Formula-III) is formed within the specified limit of <0.1%. Generally, irbesartan prepared using zinc halide or tributyltin azide requires extensive purification to remove this impurity which results in considerable yield loss.

In yet another embodiment, the present invention provides a process for complete conversion of the cyano intermediate in 6-8 hours to yield irbesartan compared with use of triethylammonium hydrochloride, where complete conversion is not observed even after long reaction time such as 18 hours.

DETAILED DESCRIPTION OF THE INVENTION

According to the present invention, there is provided a process for the preparation of 2-butyl-3-[[2'-(1H-tetrazol-5-yl)[1,1'-biphenyl]-4-yl]-1,3-diazaspiro[4,4]non-1-en-4-one (Irbesartan), which comprises:

a) reacting 2-n-butyl-3-[(2'-cyanobiphenyl-4-yl)methyl]-1,3-diazaspiro-[4,4]-non-1-en-4-one with sodium azide and piperazine or its acid salt in a suitable organic solvent and obtaining the resulting 2-butyl-3-[[2'-(1H-tetrazol-5-yl)[1,1'-biphenyl]-4-yl]-1,3-diazaspiro[4,4]non-1-en-4-one as an alkaline salt in aqueous solution;

b) neutralizing the alkaline salt solution of 2-butyl-3-[[2'-(1H-tetrazol-5-yl)[1,1'-biphenyl]-4-yl]-1,3-diazaspiro[4,4]non-1-en-4-one with an acid and isolating the precipitated irbesartan.

In the step (a) the suitable organic solvent is a polar inert aprotic solvent such as N,N-dimethylformamide, N,N-dimethylacetamide, dimethyl sulfoxide, 1-methylpyrrolidin-2-one, preferably N,N-dimethylformamide. However, nonpolar solvents such as toluene, xylene, heptanes and other hydrocarbon solvents can also be used. These non-polar solvents give lower yields and purity.

The reaction requires elevated temperature such as 110° C. to 160° C. and can be conveniently carried out at reflux temperature. Here, reflux temperature means the temperature at which the solvent refluxes or boils at atmospheric pressure. At this temperature the reaction is very fast and completes within 6-8 hours. This is another advantage of the present process. In most of the reported methods where zinc chloride or tributyltin chloride or triethylamine hydrochloride is used as catalysts, the reaction time is usually 14 to 20 hours.

For the optimum reaction, about 3 to 5 moles of sodium azide and 2 moles of piperazine dihydrochloride are required for each mole of the starting cyano compound. It was observed that even when piperazine is used directly instead of its dihydrochloride salt, reaction takes place to a satisfactory extent.

After the reaction is completed, the reaction mixture using polar aprotic solvent is diluted with water and made alkaline using 10% sodium hydroxide solution. The pH is adjusted to about 12 to obtain sodium salt of irbesartan. The reaction mass is washed with an organic solvent such as toluene, ethyl acetate, chlorinated hydrocarbons etc. This step helps in removing several minor impurities. If at step (a) a non-polar solvent such is xylene is used, the reaction mass is treated with 5% sodium hydroxide solution to extract the sodium salt of irbesartan. This alkaline solution can be taken directly to the next step without an additional step of washing with an organic solvent.

The alkaline solution is neutralized with a mineral acid such as hydrochloric acid, sulphuric acid or phosphoric acid, preferably hydrochloric acid. The pH of the neutralized solution is adjusted to 4.0 to 7.0, preferably 6.5. This step can be conveniently conducted at ambient temperature. Elevated temperature is to be avoided during neutralization step. At lower pH yields are higher but the impurities are also higher. At pH 5.0, the yield was 78% but with only 84% purity. Minimum levels of impurities were observed at pH 6.5. The reaction mass is stirred for additional 3 hours after adjusting the pH to 6.5 before filtering the product. It gives irbesartan of >98% purity. Recrystallization with ethanol gives a product of >99.9% purity as measured by HPLC. Thus, irbesartan by the present process is obtained with high purity without using column chromatography or repeated crystallization steps for purification.

According to another aspect of the present invention there is provided a process for preparing pure 2-butyl-3-[[2'-(1H-tetrazol-5-yl)[1,1'-biphenyl]-4-yl]-1,3-diazaspiro[4,4]non-1-en-4-one, which has less than 0.1% of 2-n-butyl-3-[(2'-carboxamidobiphenyl-4-yl)methyl]-1,3-diazaspiro-[4,4]-non-1-en-4-one, the major impurity.

Another advantage of the present invention is avoiding tin reagents as catalyst used frequently in prior art processes for irbesartan.

The details of the present invention are given in the following examples, which are provided to illustrate the invention and should not be construed in any way to limit the scope of the present invention.

EXAMPLE-1

A mixture of 2-n-butyl-3-[(2'-cyanobiphenyl-4-yl)methyl]-1,3-diazaspiro-[4,4]-non-1-en-4-one (10 g), sodium azide (7.7 g) and piperazine dihydrochloride (7.5 g) in N,N-dimethylformamide (30 ml) was refluxed for 7 hours under stirring. The reaction was cooled to room temperature and 20 ml water was added. The reaction mixture was adjusted to pH of about 12 using 10% NaOH solution. The alkaline solution was washed with toluene (15 ml) and the aqueous phase was neutralized to pH of 6.5 using concentrated HCl. The resulting suspension was stirred for 3 hours at room temperature and filtered to obtain irbesartan (5.8 g, 98% purity by HPLC). Recrystallization of the Product using ethanol results in 5.2 g of irbesartan with 99.94% purity and content of the impurity 2-n-butyl-3-[(2'-carboxamidobiphenyl-4-yl)methyl]-1,3-diazaspiro-[4,4]-non-1-en-4-one: 0.07%.

EXAMPLE-2

A mixture of 2-n-butyl-3-[(2'-cyanobiphenyl-4-yl)methyl]-1,3-diazaspiro-[4,4]-non-1-en-4-one (10g), sodium azide (7.7 g) and piperazine dihydrochloride (7.5 g) in N,N-dimethylformamide (30 ml) was refluxed for 7 hours under stirring. The reaction was cooled to room temperature and 20 ml water was added. The reaction mixture was adjusted to pH of about 12 using 10% NaOH solution. The alkaline solution was washed with toluene (15 ml) and the aqueous phase was neutralized to pH of 6.0 using concentrated HCl. The resulting suspension was stirred for 3 hours at room temperature and filtered to obtain irbesartan (6.0 g, 92.7% purity by HPLC) and content of the impurity 2-n-butyl-3-[(2'-carboxamidobiphenyl-4-yl)methyl]-1,3-diazaspiro-[4,4]-non-1-en-1-one 0.07%. When the pH was adjusted to 5.6, the yield remained same but the purity was further reduced to 90.2% and content of the impurity 2-n-butyl-3-[(2'-carboxamidobiphenyl-4-yl)methyl]-1,3-diazaspiro-[4,4]-non-1-ene-4-one; 0.09%.

EXAMPLE-3

A mixture of 2-n-butyl-3-[(2'-cyanobiphenyl-4-yl)methyl]-1,3-diazaspiro-[4,4]-non-1-en-4-one (10 g), sodium azide (7.7 g) and piperazine (10.2 g) in 1-methylpyrrolidin-2-one (30 ml) was refluxed for 7 hours under stirring. The reaction was cooled to room temperature and 20 ml water was added. The reaction mixture was adjusted to pH of about 12 using 10% NaOH solution. The alkaline solution was washed with toluene (15 ml) and the aqueous phase was neutralized to pH of 6.5 using concentrated HCl. The resulting suspension was stirred for 3 hours at room temperature and filtered to obtain irbesartan (2.5 g, 94.4% purity by HPLC).

EXAMPLE-4

A mixture of 2-n-butyl-3-[(2'-cyanobiphenyl-4-yl)methyl]-1,3-diazaspiro-[4,4]-non-1-en-4-one (10 g), sodium azide (7.7 g) and piperazine dihydrochloride (7.5 g) in xylene (30 ml) was refluxed for 7 hours under stirring. The reaction was cooled to room temperature and extracted with 5% NaOH solution. The pooled alkaline solution was washed with toluene or xylene (15 ml) and the aqueous phase neutralized to pH 6.5 using concentrated HCL. The resulting suspension was stirred for 3 hours at room temperature and filtered obtain irbesartan (3.6 g, 96% purity by HPLC).

EXAMPLE-5

Using Triethylamine Hydrochloride and DMF

A mixture of 2-n-butyl-3-[(2'-cyanobiphenyl-4-yl)methyl]-1,3-diazaspiro-[4,4]-non-1-en-4-one (10 g), sodium azide (7.7 g) and triethylamine hydrochloride (7.1 g) in N,N-dimethylformamide (30 ml) was refluxed for 14 hours under stirring. The reaction was cooled to room temperature and 20 ml water was added. The reaction mixture was adjusted to pH of about 12 using 10% NaOH solution. The alkaline solution was washed with toluene (15 ml) and the aqueous phase was neutralized to pH of 6.5 using concentrated HCl. The resulting suspension was stirred for 3 hours at room temperature and filtered to obtain irbesartan (3.4 g, 95% purity by HPLC). Recrystallization of the product using ethanol results in 3.05 g of irbesartan with 99.2% purity and content of the impurity 2-n-butyl-3-[(2'-carboxamidobiphenyl-4-yl)methyl]-1,3-diazaspiro-[4,4]-non-1-en-4-one: 0.09%.

EXAMPLE-6

Using TriethylamineHCl and NMP

This example was performed as in example-5 but by changing the solvent to N-methylpyrrolidone, increasing triethylamine hydrochloride from 2.18 to 5 equivalents, and increasing the reaction time to 24 hours. However this did not result in the completion of the reaction or improve the yield.

We claim:

1. A process for the preparation of 2-butyl-3-[[2'-(1H-tetrazol-5-yl)[1,1'-biphenyl]-4-yl]-1,3-diazaspiro[4,4]non-1-en-4-one (Irbesartan), which comprises:
    a) reacting 2-n-butyl-3-[(2'-cyanobiphenyl-4-yl)methyl]-1,3-diazaspiro-[4,4]-non-1-en-4-one with sodium azide and piperazine or its acid salt in a suitable organic solvent and obtaining the resulting 2-butyl-3-[[2'-(1H-tetrazol-5-yl)[1,1'-biphenyl]-4-yl]-1,3-diazaspiro[4,4]non-1-en-4-one as an alkaline salt in aqueous solution;
    b) neutralizing the alkaline salt solution of 2-butyl-3-[[2'-(1H-tetrazol-5-yl)(1,1'-biphenyl]-4-yl]-1,3-diazaspiro[4,4]non-1-en-4-one with an acid and isolating the precipitated irbesartan.

2. The process according to claim-1, step-a, wherein the organic solvent is selected from the group consisting of N,N-dimethylformamide, N,N-dimethylacetamide, dimethyl sulfoxide, 1-methylpyrrolidin-2-one, toluene, xylene or mixtures thereof, preferably N,N-dimethylformamide.

3. The process according to claim-1, step-b, wherein the alkaline solution is neutralized using a mineral acid selected from the group consisting of hydrochloric acid, sulphuric acid, and phosphoric acid preferably hydrochloric acid.

4. The process according to claim-3, wherein the alkaline solution is neutralized to a pH 4.0 to 7.0, preferably 6.0 to 6.5.

5. The process according to claim-1 wherein irbesartan obtained is substantially free from 2-n-butyl-3-[(2'-carboxamidobiphenyl-4-yl)methyl]-1,3-diazaspiro-[4,4]-non-1-en-4-one.

* * * * *